US006576256B2

(12) United States Patent
Liang et al.

(10) Patent No.: US 6,576,256 B2
(45) Date of Patent: Jun. 10, 2003

(54) TREATMENT OF PATIENTS AT ELEVATED CARDIOVASCULAR RISK WITH A COMBINATION OF A CHOLESTEROL-LOWERING AGENT, AN INHIBITOR OF THE RENIN-ANGIOTENSIN SYSTEM, AND ASPIRIN

(75) Inventors: Matthew H. Liang, Boston, MA (US); JoAnn E. Manson, Beverly, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 09/942,084

(22) Filed: Aug. 28, 2001

(65) Prior Publication Data

US 2003/0049314 A1 Mar. 13, 2003

(51) Int. Cl.[7] .............................. A61K 9/48; A61K 9/00; A61K 9/64; A61K 9/20; A61K 9/14
(52) U.S. Cl. ....................... 424/451; 424/400; 424/456; 424/464; 424/465; 424/489
(58) Field of Search ................................. 424/464, 489, 424/465, 452, 400, 456

(56) References Cited

U.S. PATENT DOCUMENTS

| 4,795,433 A | * | 1/1989 | Sarnoff |
| 5,140,012 A | | 8/1992 | McGovern et al. |
| 5,157,025 A | | 10/1992 | Aberg et al. |
| H1286 H | | 2/1994 | Eisman et al. |
| 5,298,497 A | | 3/1994 | Tschollar et al. |
| 5,461,039 A | | 10/1995 | Tschollar et al. |
| 5,593,971 A | | 1/1997 | Tschollar et al. |
| 5,622,985 A | | 4/1997 | Olukotun et al. |
| 5,668,117 A | * | 9/1997 | Shapiro |
| 6,235,311 B1 | | 5/2001 | Ullah et al. |
| 6,248,729 B1 | * | 6/2001 | Coniglio et al. |
| 6,251,852 B1 | | 6/2001 | Gould et al. |
| 6,274,170 B1 | * | 8/2001 | Heibel et al. |

FOREIGN PATENT DOCUMENTS

| EP | 0457514 | 8/1996 |
| EP | 0622078 | 9/1999 |
| WO | WO 01/15674 | 3/2001 |

OTHER PUBLICATIONS

Fonarow et al. (2000), "Rationale and Design of the Cardiac Hospitalization Atherosclerosis Management Program at the University of California Los Angeles," *Am. J. Cardiol.* 85:10A–17A.

Fonarow et al. (2001), "Improved Treatment of Coronary Heart Disease by Implementation of a Cardiac Hospitalization Atherosclerosis Management Program (CHAMP)," *Am. J. Cardiol.* 87:819–822.

* cited by examiner

*Primary Examiner*—Thurman K. Page
*Assistant Examiner*—Simon J. Oh
(74) *Attorney, Agent, or Firm*—Dianne E. Reed; Karen Canaan; Reed & Eberle LLP

(57) ABSTRACT

Methods and compositions are provided for reducing the risk of cardiovascular events in individuals who are at elevated cardiovascular risk, including individuals who have systemic lupus erythematosus. The methods comprise administering a combination of: a cholesterol-lowering agent, such as an HMG CoA reductase inhibitor; an inhibitor of the renin-angiotensin system, such as an ACE inhibitor; aspirin; and optionally one or more of vitamin $B_6$, vitamin $B_{12}$, and folic acid. Pharmaceutical formulations combining all the active agents in unit-dose form for once-daily dosing are provided.

52 Claims, No Drawings

TREATMENT OF PATIENTS AT ELEVATED CARDIOVASCULAR RISK WITH A COMBINATION OF A CHOLESTEROL-LOWERING AGENT, AN INHIBITOR OF THE RENIN-ANGIOTENSIN SYSTEM, AND ASPIRIN

TECHNICAL FIELD

This invention relates generally to methods and pharmaceutical formulations for treating patients at elevated cardiovascular risk, and more particularly relates to treatment of such patients with a combination of a cholesterol-lowering agent, an inhibitor of the renin-angiotensin system, and aspirin.

BACKGROUND

Many individuals are at an elevated risk of suffering serious to life-threatening cardiovascular events, such as myocardial infarction (heart attack), cardiac arrest, congestive heart failure, stroke, peripheral vascular disease and/or claudication. The risk factors are numerous and widespread throughout the world population. They include cigarette smoking, diabetes, hypercholesterolemia (high serum cholesterol), hypertension, angina, systemic lupus erythematosus, prior heart attacks or strokes, hemodialysis, hyperhomocysteine levels, obesity, sedentary lifestyle, receiving an organ transplant, and others. Many of these risk factors are mediated through atherosclerosis. There is a need for a safe and convenient pharmaceutical formulation that would effectively reduce the risk of incurring a cardiovascular event in individuals who have these risk factors.

Olukotun et al., in U.S. Pat. No. 5,622,985, disclose that inhibitors of 3-hydroxy-3-methylglutaryl coenzyme A (HMG CoA) reductase (cholesterol-lowering drugs), particularly pravastatin, when used alone or with an angiotensin converting enzyme (ACE) inhibitor, decrease the risk of a second heart attack in a patient who has a substantially normal cholesterol level. The combination with an ACE inhibitor is optional, and no mention is made of combining HMG CoA reductase inhibitors with other inhibitors of the renin-angiotensin system or with aspirin. In addition, the prevention of cardiovascular events other than second heart attacks is not considered.

Similarly, McGovern et al., in U.S. Pat. No. 5,140,012, disclose the use of pravastatin alone, or in combination with an ACE inhibitor, to prevent the onset of restenosis following angioplasty. HMG CoA reductase inhibitors other than pravastatin are not considered, and no mention is made of combining HMG CoA reductase inhibitors with other inhibitors of the renin-angiotensin system or with aspirin. The prevention of cardiovascular disorders other than restenosis following angioplasty is not considered.

U.S. Pat. Nos. 5,461,039 and 5,593,971 to Tschollar et al. disclose the use of a cholesterol-lowering drug, alone or in combination with an ACE inhibitor, to inhibit hypertension in a normotensive individual who has insulin resistance. No mention is made of combining cholesterol-lowering drugs with inhibitors of the renin-angiotensin system other than ACE inhibitors or with aspirin. In addition, the disclosed methods are limited to normotensive individuals who are insulin resistant, and no mention is made of directly preventing cardiovascular events.

Eisman et al., in U.S. Statutory Invention Registration No. H1286, disclose a method for treating peripheral atherosclerotic disease and/or intermittent claudication by use of one or more cholesterol-lowering drugs by themselves or together with an ACE inhibitor, or by use of an ACE inhibitor alone. No mention is made of combining cholesterol-lowering drugs with inhibitors of the renin-angiotensin system other than ACE inhibitors or with aspirin. The treatment or prevention of cardiovascular disorders other than peripheral atherosclerotic disease and/or intermittent claudication is not considered.

Bergey et al., in European Patent Specification EP 0 457,514 B1, disclose the use of a cholesterol-lowering drug together with an ACE inhibitor to prevent, stabilize, or cause regression of atherosclerosis. No mention is made of combining cholesterol-lowering drugs with inhibitors of the renin-angiotensin system other than ACE inhibitors or with aspirin. The treatment or prevention of cardiovascular disorders other than atherosclerosis is not considered.

U.S. Pat. No. 6,235,311 to Ullah et al. discloses pharmaceutical compositions containing a statin (HMG CoA reductase inhibitor) plus aspirin, optionally containing vitamins $B_6$, $B_{12}$, or folic acid, and methods of their use for: lowering serum cholesterol; preventing, inhibiting, or treating atherosclerosis; or reducing the risk of or treating a cardiovascular event or disease, coronary artery disease, or cerebrovascular disease. This reference makes no mention of, or considers in any way, inhibitors of the renin-angiotensin system.

Coniglio et al., in U.S. Pat. No. 6,248,729, disclose a method for preventing a cerebral infarction by administering to a patient a combination of an ADP-receptor blocking antiplatelet drug, an antihypertensive agent (such as an angiotensin II antagonist, an ACE inhibitor, or an ACE/NEP inhibitor), and optionally aspirin. Pharmaceutical compositions comprising combinations of these agents are also disclosed. The disclosed methods and compositions, however, require an ADP-receptor blocking antiplatelet drug (which does not include aspirin) and do not mention or consider cardiovascular events other than a cerebral infarction.

Schoelkens et al., in International Patent Publication No. WO 01/15674, disclose the use of an inhibitor of the renin-angiotensin system, optionally together with another antihypertensive drug, a cholesterol-lowering drug, a diuretic, or aspirin, in the prevention of cardiovascular events. Also disclosed is a combination product for this purpose containing an inhibitor of the renin-angiotensin system and a cholesterol-lowering agent. Further disclosed is the use of an inhibitor of the renin-angiotensin system together with another antihypertensive, or a cholesterol-lowering agent, or a diuretic, or aspirin in the manufacture of a medicament for the prevention of cardiovascular events. Never mentioned or considered is the possibility of combining three or more active agents, either in a method for the treatment of a patient or in the manufacture of a pharmaceutical product. Even though certain inhibitors of the renin-angiotensin system, cholesterol-lowering agents, and aspirin are mentioned, and combination therapies involving inhibitors of the renin-angiotensin system together with a cholesterol-lowering agent or aspirin are disclosed, no consideration is made of combining all three.

SUMMARY OF THE INVENTION

Accordingly, it is a primary object of the invention to provide a pharmaceutical composition that overcomes the limitations of the above-described formulations and dosage forms.

One object of the invention is to provide a method for treating a patient at elevated cardiovascular risk, such method involving the daily oral administration of a pharmaceutical composition, preferably a single pharmaceutical composition, containing therapeutically effective unit dosages of a cholesterol-lowering agent, an inhibitor of the renin-angiotensin system, aspirin, and optionally one or more B vitamins.

Another object of the invention is to provide such a method wherein the elevated cardiovascular risk as is an elevated risk of cardiac arrest, myocardial infarction (including acute or chronic myocardial infarction), coronary heart disease, ischemia, stroke, claudication, peripheral vascular disease, restenosis, and/or atherosclerosis.

Still another object of the invention is to provide such a method wherein the patient at elevated cardiovascular risk has systemic lupus erythematosus, is or has been a cigarette smoker, is diabetic, is on hemodialysis, or has received an organ transplant.

Still another object of the invention is to provide such a method wherein the cholesterol-lowering agent is an HMG CoA reductase inhibitor, the inhibitor of the renin-angiotensin system is an ACE inhibitor or an angiotensin II antagonist, and the composition contains vitamin $B_6$, vitamin $B_{12}$, and folic acid.

Yet another object of the invention is to provide a method for increasing the likelihood that a patient suffering an acute myocardial infarction (MI) will survive, the method comprising administering the pharmaceutical composition to the patient at the time of the MI.

It is another object of the invention is to provide a once-daily orally administrable pharmaceutical composition for treating a patient at elevated cardiovascular risk, the composition comprising a combination of therapeutically effective unit dosages of a cholesterol-lowering agent, an inhibitor of the renin-angiotensin system, aspirin, and optionally one or more of vitamin $B_6$, vitamin $B_{12}$, and folic acid, plus a pharmaceutically acceptable carrier, wherein each unit dosage is a daily dose.

Another object of the invention is to provide such compositions wherein the cholesterol-lowering agent is an HMG CoA reductase inhibitor and the inhibitor of the renin-angiotensin system is an ACE inhibitor or an angiotensin II antagonist.

It is still another object of the invention to provide such compositions wherein all three of vitamin $B_6$, vitamin $B_{12}$, and folic acid are incorporated therein.

Additional objects, advantages and novel features of the invention will be set forth in part in the description which follows, and in part will become apparent to those skilled in the art upon examination of the following, or may be learned by practice of the invention.

The present invention provides a once-daily oral dosage form containing a combination of a therapeutically effective unit dose of a cholesterol-lowering agent, a therapeutically effective unit dose of an inhibitor of the renin-angiotensin system, and a therapeutically effective unit dose of aspirin, optionally further combined with at least one vitamin B substance, and a method for treating a patient at elevated cardiovascular risk by administering the dosage form on a daily basis. Prior to the present invention, patients at elevated cardiovascular risk lacked adequate treatment to reduce their risk of cardiovascular events due to the unavailability of effective, safe, and convenient drugs for this purpose. The present invention, by contrast, provides a safe and effective method for reducing the risk of cardiovascular events in these patients, by providing a single oral dosage form containing the aforementioned combination of active agents, which is conveniently administered once per day. Such a simple regimen has a high degree of patient compliance, leading to substantially improved efficacy. The combination of three or more active ingredients provides the additional advantage of possibly allowing reduced dosages of the active ingredients, increasing the safety of the therapy.

In a preferred embodiment, the dosage form of the invention comprises:

approximately 10 mg to approximately 80 mg, preferably approximately 25 mg to approximately 60 mg, of an HMG CoA reductase inhibitor selected from the group consisting of atorvastatin, fluvastatin, lovastatin, pravastatin, and simvastatin;

approximately 1 mg to approximately 20 mg, preferably approximately 5 mg to approximately 15 mg, of an ACE inhibitor selected from the group consisting of captopril, enalapril, fosinopril, lisinopril, quinapril, ramipril, and trandolapril;

approximately 20 mg to approximately 600 mg, preferably approximately 20 mg to approximately 150 mg, of aspirin; and, optionally, at least one of approximately 25 mg to approximately 75 mg, preferably approximately 40 mg to approximately 60 mg, of vitamin $B_6$;

approximately 0.25 mg to approximately 2 mg, preferably approximately 0.5 mg to approximately 1.5 mg, of vitamin $B_{12}$; and approximately 0.5 mg to approximately 8 mg, preferably approximately 1.5 mg to approximately 5 mg, of folic acid.

DETAILED DESCRIPTION OF THE INVENTION

I. DEFINITIONS AND NOMENCLATURE

Before describing the present invention in detail, it is to be understood that this invention is not limited to specific dosage forms, carriers, or the like, as such may vary. It is also to be understood that the terminology used herein is for the purpose of describing particular embodiments only, and is not intended to be limiting.

It must be noted that as used in this specification and the appended claims, the singular forms "a," "an", and "the" include plural referents unless the context clearly dictates otherwise. Thus, for example, reference to "an active agent" or "a pharmacologically active agent" includes a single active agent as well as two or more different active agents in combination, reference to "a carrier" includes mixtures of two or more carriers as well as a single carrier, and the like.

In describing and claiming the present invention, the following terminology will be used in accordance with the definitions set out below.

The terms "active agent," "pharmacologically active agent" and "drug" are used interchangeably herein to refer to a chemical compound that induces a desired pharmacological, physiological effect. The primary active agents herein are cholesterol-lowering agents, inhibitors of the renin-angiotensin system, and aspirin. The terms also encompass pharmaceutically acceptable, pharmacologically active derivatives of those active agents specifically mentioned herein, including, but not limited to, salts, esters, amides, prodrugs, active metabolites, analogs, and the like. When the terms "active agent," "pharmacologically active agent" and "drug" are used, then, or when an active agent such as an HMG CoA reductase inhibitor or an ACE inhibitor is specifically identified, it is to be understood that applicants intend to include the active agent per se as well as pharmaceutically acceptable, pharmacologically active salts, esters, amides, prodrugs, metabolites, analogs, etc.

The terms "cholesterol-lowering agent" and "cholesterol-lowering drug" as used herein refer to a pharmacologically active, pharmaceutically acceptable agent that, when administered to a human subject who has hypercholesterolemia, has the effect of beneficially modifying serum cholesterol levels. More particularly, the cholesterol-lowering agent lowers serum low density lipoprotein (LDL) cholesterol levels, or inhibits oxidation of LDL cholesterol, whereas high density lipoprotein (HDL) serum cholesterol levels may be lowered, remain the same, or be increased. Preferably, the cholesterol-lowering agent brings the serum levels of LDL cholesterol and HDL cholesterol (and, more preferably, triglyceride levels) to normal or nearly normal levels.

The term "inhibitor of the renin-angiotensin system" as used herein refers to a pharmacologically active, pharmaceutically acceptable agent that inhibits, directly or indirectly, the adverse effects of angiotensin, particularly angiotensin II. Included, without limitation, are agents that: inhibit angiotensin II synthesis; inhibit angiotensin II binding to the $AT_1$ receptor; or inhibit renin activity.

By "pharmaceutically acceptable," such as in the recitation of a "pharmaceutically acceptable carrier," or a "pharmaceutically acceptable acid addition salt," is meant herein a material that is not biologically or otherwise undesirable, i.e., the material may be incorporated into a pharmaceutical composition administered to a patient without causing any undesirable biological effects or interacting in a deleterious manner with any of the other components of the composition in which it is contained. "Pharmacologically active" (or simply "active"), as in a "pharmacologically active" derivative or metabolite, refers to a derivative or metabolite having the same type of pharmacological activity as the parent compound and approximately equivalent in degree. When the term "pharmaceutically acceptable" is used to refer to a derivative (e.g., a salt) of an active agent, it is to be understood that the compound is pharmacologically active as well, i.e., therapeutically effective to reduce elevated cardiovascular risk.

"Carriers" or "vehicles" as used herein refer to conventional pharmaceutically acceptable carrier materials suitable for drug administration, and include any such materials known in the art that are nontoxic and do not interact with other components of a pharmaceutical composition or drug delivery system in a deleterious manner.

By an "effective" amount or a "therapeutically effective amount" of a drug or pharmacologically active agent is meant a nontoxic but sufficient amount of the drug or agent to provide the desired effect. In the combination therapy of the present invention, an "effective amount" of one component of the combination is the amount of that compound that is effective to provide the desired effect when used in combination with the other components of the combination. The amount that is "effective" will vary from subject to subject, depending on the age and general condition of the individual, the particular active agent or agents, and the like. Thus, it is not always possible to specify an exact "effective amount." However, an appropriate "effective" amount in any individual case may be determined by one of ordinary skill in the art using routine experimentation.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. Thus, for example, "treating" a patient involves prevention of a particular disorder or adverse physiological event in a susceptible individual as well as treatment of a clinically symptomatic individual.

The term "elevated cardiovascular risk" as used herein refers to an increased risk of incurring a cardiovascular event, peripheral vascular disease, coronary heart disease, restenosis, or atherosclerosis in an individual, such risk being due to disorders, diseases, genetic factors, behaviors, diets, or other conditions or factors. The conditions or factors that lead to elevated cardiovascular risk include, without limitation: systemic lupus erythematosus, current or prior cigarette smoking, diabetes, hemodialysis, receiving an organ transplant, manifest coronary artery disease, history of myocardial infarction, history of transient ischemic attacks or stroke, history of peripheral vascular disease, angina, hypertension, hypercholesterolemia, obesity, atherosclerosis, kidney disease, Chlamydia infection, Bartonella infection, and obstructive pulmonary disease.

The term "cardiovascular event" as used herein refers to a disorder or disease of the cardiovascular system having a rather sudden onset; it can also refer to a rather sudden worsening of such a disorder or disease. Examples of cardiovascular events include, without limitation: cardiac arrest, myocardial infarction, ischemia, stroke, worsening of angina, and congestive heart failure.

II. THE ACTIVE AGENTS

A. CHOLESTEROL-LOWERING AGENTS

This invention employs any effective cholesterol-lowering agent or combination of such agents. Preferred cholesterol-lowering agents are HMG CoA reductase inhibitors, bile acid sequestrants, probucol, and fibric acid agents. Particularly preferred are HMG CoA reductase inhibitors, especially atorvastatin, cerivistatin, fluindostatin, fluvastatin, lovastatin, mevastatin, pravastatin, simvastatin, and velostatin; the most preferred agents are lovastatin and pravastatin, particularly pravastatin. Cholesterol-lowering agents are well known in the art and are discussed and reviewed in numerous publications; a useful review is presented by Witztum, J. L., "Drugs used in the treatment of hyperlipidemia", in Hardman, J. G., Gilman, A. G., and Limbird, L. E., editors, Goodman and Gilman's The Pharmacological Basis of Therapeutics, 9th Edition, pp. 875–897 (New York: McGraw-Hill, 1996). Brief descriptions of some of the classes of cholesterol-lowering agents that may be used in this invention follow.

HMG CoA reductase inhibitors: The members of this class of compounds inhibit 3-hydroxy-3-methylglutaryl coenzyme A (HMG CoA) reductase. This enzyme catalyzes the conversion of HMG CoA to mevalonate, which is an early and rate-limiting step in the biosynthesis of cholesterol. Examples of HMG CoA reductase inhibitors that may be used include but are not limited to lovastatin (MEVACOR™; see U.S. Pat. No. 4,231,938), simvastatin (ZOCOR™; see U.S. Pat. No. 4,444,784), pravastatin (PRAVACHOL™; see U.S. Pat. No. 4,346,227), fluvastatin (LESCOL™; see U.S. Pat. No. 5,354,772), atorvastatin (LIPITOR™; see U.S. Pat. No. 5,273,995), cerivastatin (also called rivastatin; see U.S. Pat. No. 5,177,080), mevastatin (see U.S. Pat. No. 3,883,140), fluindostatin (Sandoz XU-62-320), velostatin (also called synvinolin; see U.S. Pat. Nos. 4,448,784 and 4,450,171), and compounds related to these as described in the cited references. Some other examples of HMG CoA reductase inhibitors that may be used are, without limitation, presented in U.S. Pat. No. 6,264,938 at Table 1 and U.S. Pat. No. 5,622,985, columns 3 through 6. All pharmaceutically acceptable HMG CoA reductase inhibitors are included in this invention. Compounds that inhibit the activity of HMG CoA reductase can be readily identified by using assays well known in the art; see, as examples, the assays described or cited in U.S. Pat. No. 4,231,938 at column 6, and in International Patent Publication WO 84/02131 at pp. 30–33. The term "HMG CoA reductase inhibitor" is intended to include all pharmaceutically acceptable salt, ester, and lactone forms of compounds that have HMG CoA reductase inhibitory activity, and therefore the use of such salt, ester, and lactone forms is included within the scope of this invention.

HMG CoA reductase inhibitors are particularly preferred cholesterol-lowering agents herein, insofar as they tend to exhibit fewer undesirable side effects than other cholesterol lowering agents, are more desirable in terms of safety and tolerance issues, do not need to be titrated, and exhibit one or more beneficial effects in addition to lowering cholesterol, e.g., a reduction in bone loss.

Bile acid sequestrants: Bile acids, which are secreted into the intestine to aid in the digestion and absorption of lipids, are synthesized in the liver from cholesterol. Normally, approximately 97% of bile acids are reabsorbed and reused. If large amounts of bile acids are excreted, then the liver must convert more cholesterol to bile acids, lowering serum cholesterol levels, particularly LDL cholesterol levels. Although biosynthesis of cholesterol is up-regulated in this case, the net effect of increased bile acid synthesis in most individuals is to lower cholesterol, particularly LDL cholesterol, levels in the serum.

Bile acid sequestrants are poorly absorbed resins or other substances that bind to and sequester bile acids in the intestine. The sequestered bile acids are subsequently excreted in the feces. Any pharmaceutically acceptable bile acid sequestrant may be used in the practice of this invention. Examples of bile acid sequestrants that may be used in this invention include, without limitation, cholestyramine, colesevelam, colestipol, poly[methyl-(3-trimethylaminopropyl)imino-trimethylene dihalide], and those disclosed in U.S. Pat. No. 6,271,264, International Patent Publication WO 95/34585, and European Patent Publication No. EP 0 622,078.

Probucol: This compound is a potent lipophilic antioxidant that inhibits the oxidation of LDL cholesterol. As the oxidation of LDL cholesterol may be an important, and perhaps essential, factor in the development of atherosclerotic lesions, probucol may be useful in preventing or treating atherosclerosis. Although probucol is known to lower serum cholesterol levels, the mechanism of action is not well understood. Probucol is often useful in treating patients who do not respond to other cholesterol-lowering drugs, such as patients with homozygous familial hypercholesterolemia.

Fibric acid derivatives: These compounds, also known as "fibrates," lower triglyceride levels, raise high density lipoprotein (HDL) levels, and have variable effects on LDL cholesterol levels in the blood. Examples of fibric acid derivatives that may be used in this invention include, without limitation, bezafibrate (Bezalip™), beclobrate, binifibrate, ciprofibrate, clinofibrate, clofibrate, etofibrate, fenofibrate (Lipidil™ Lipidil Micro™), gemfibrozil (Lopid™), nicofibrate, pirifibrate, ronifibrate, simfibrate, and theofibrate.

B. INHIBITORS OF THE RENIN-ANGIOTENSIN SYSTEM

The renin-angiotensin system plays a major role in regulating blood pressure. Renin, an enzyme synthesized, stored, and secreted by the kidneys, potently increases blood pressure; normally, its secretion increases when blood pressure is low and decreases when blood pressure is high. Renin functions by acting on angiotensinogen to form the decapeptide angiotensin I. Angiotensin I is rapidly converted to the octapeptide angiotensin II by angiotensin converting enzyme (ACE). Angiotensin II acts by numerous mechanisms to raise blood pressure, including raising total peripheral resistance (in part by constricting precapillary arterioles and, to a lesser extent, postcapillary venules; by enhancing peripheral noradrenergic neurotransmission; and by central nervous system effects), reducing sodium excretion while increasing potassium excretion by the kidneys, and increasing aldosterone secretion by the adrenal cortex (aldosterone acts to retain sodium and to excrete potassium and hydrogen ions). Angiotensin II is also believed to contribute to pathological structural changes in the cardiovascular system, including cardiac hypertrophy (excessive tissue mass), cardiac fibrosis (associated with congestive heart failure and myocardial infarction), and thickening of the intimal surface of blood vessel walls (associated with atherosclerosis).

Drugs to lower blood pressure have been developed that successfully target several pathways in the renin-angiotensin system. Best known and most widely used are the ACE inhibitors, which inhibit the conversion of angiotensin I to angiotensin II. Also developed are angiotensin II receptor antagonists and renin inhibitors. These classes of drugs are briefly discussed below; much more information is readily available in published literature (see, for example, the review by Jackson, E. K. and Garrison, J. C., in Hardman, J. G., Gilman, A. G., and Limbird, L. E., editors, Goodman and Gilman's The Pharmacological Basis of Therapeutics, 9th Edition, pp. 733–754 (New York: McGraw-Hill, 1996). ACE inhibitors are the preferred inhibitors of the renin-angiotensin system for use in conjunction with the present compositions and methods. It should also be noted that in addition to lowering blood pressure, ACE inhibitors reduce plasma levels of TGF-β, an added benefit in many patients, e.g., those suffering from systemic lupus erythematosus.

Angiotensin converting enzyme (ACE) inhibitors: As mentioned, ACE inhibitors inhibit the conversion of angiotensin I to angiotensin II. Because angiotensin I has only about 1% of the hypertensive activity of angiotensin II, ACE inhibitors are generally effective in reducing blood pressure and the other adverse cardiovascular effects caused by angiotensin II. ACE has numerous substrates other than angiotensin I, including bradykinin. By interfering with the conversion of bradykinin, ACE inhibitors increase bradykinin levels; this mechanism may contribute to the efficacy of ACE inhibitors.

Also included in this invention are ACE/NEP inhibitors, which are ACE inhibitors that also have an inhibitory effect on neutral endopeptidase (NEP), an enzyme that degrades atrial natriuretic peptide. Inhibition of NEP may be particularly effective in controlling volume-expanded hypertension.

Numerous ACE inhibitors have been synthesized. Most of these compounds can be classified into three groups based on their chemical structure: (1) sulfhydryl-(also called mercapto-) containing ACE inhibitors, including captopril and agents that are structurally related to captopril, such as fentiapril, pivalopril, zofenopril and alacepril; (2) dicarboxyl-containing ACE inhibitors, including enalapril and agents that are structurally related to enalapril, such as lisinopril, benazepril, quinapril, moexipril, ramipril, spirapril, perindopril, indolapril, pentopril, indalapril and cilazapril; and (3) phosphorus-containing ACE inhibitors, structurally related to fosinopril. Many of the ACE inhibitors are esters developed for high oral bioavailability, but with low potency in themselves; they must be converted to particular metabolites in the body that have potent activity.

ACE inhibitors are well known in the art, and the use of any pharmaceutically acceptable ACE inhibitor, including any of those mentioned in the preceding paragraph, is included in this invention, including mixtures thereof and/or their pharmaceutically acceptable salts. Some further examples of ACE inhibitors that may be used in the practice of this invention are, without limitation, AB-103, ancovenin, benazeprilat, BRL-36378, BW-A575C, CGS13928C, CL242817, CV-5975, Equaten, EU-4865, EU-4867, EU-5476, foroxymithine, FPL 66564, FR-900456, Hoe-065, 15B2, indolapril, ketomethylureas, KRI-1177, KRI-1230, L681176, libenzapril, MCD, MDL-27088, MDL-27467A, moveltipril, MS-41, nicotianamine, pentopril, phenacein, pivopril, rentiapril, RG-5975, RG-6134, RG-6207, RGH0399, ROO-911, RS-10085-197, RS-2039, RS 5139, RS-86127, RU-44403, S-8308, SA-291, spiraprilat, SQ26900, SQ-28084, SQ-28370, SQ-28940, SQ-31440, Synecor, utibapril, WF-10129, Wy-44221, Wy-44655, Y23785, Yissum, P-0154, zabicipril, Asahi Brewery AB-47, alatriopril, BMS 182657, Asahi Chemical C-111, Asahi Chemical C-112, Dainippon DU-1777, mixanpril, Prentyl, zofenoprilat, 1(- (1-carboxy-6- (4-piperidinyl) hexyl) amino)-1-oxopropyl octahydro-IH-indole-2-carboxylic acid, Bioproject BP1.137, Chiesi CHF 1514, Fisons FPL-66564, idrapril, perindoprilat, Servier S-5590, alacepril, benazepril, captopril, cilazapril, delapril, enalapril, enalaprilat, fosinopril, fosinoprilat, imidapril, lisinopril, perindopril, quinapril, ramipril, ramiprilat, saralasin acetate, temocapril, trandolapril, trandolaprilat, ceranapril, moexipril, quinaprilat, spirapril, and those listed in U.S. Pat. No. 6,248,729.

Preferred ACE inhibitors are captopril, cilazapril, delapril, enalapril, fentiapril, fosinopril, indolapril, lisinopril, perindopril, pivopril, quinapril, ramipril, spirapril, trandolapril, and zofenopril; particularly preferred are captopril, enalapril, fosinopril, lisinopril, quinapril, ramipril, and trandolapril; and most preferred is ramipril.

Some examples of ACE/NEP inhibitors for use herein include, without limitation, those disclosed in U.S. Pat. Nos. 5,508,272, 5,362,727, 5,366,973, 5,225,401, 4,722,810, 5,223,516, 5,552,397, 4,749,688, 5,504,080, 5,612,359, and 5,525,723, and European Patent Applications 0481,522, 0534363A2, 534,396, and 534,492. Preferred are those ACE/NEP inhibitors that are designated as preferred in the above U.S. patents. Particularly preferred are the ACE/NEP inhibitors omapatrilat (disclosed in U.S. Pat. No. 5,508,272) and MDL100240 (disclosed in U.S. Pat. No. 5,430,145).

Angiotensin II receptor antagonists (also known as angiotensin II antagonists): Angiotensin II binds to angiotensin subtype I ($AT_1$) and subtype 2 ($AT_2$) receptors, as well as to several other receptors. All the known physiological effects of angiotensin II are apparently due to its binding to, and activation of, the $AT_1$ receptor, which is abundantly expressed in the tissues affected by angiotensin II. $AT_2$ receptor is common in some fetal tissues but is scarce in adult tissues; to date, no known function has been discovered for it. Many orally active, nonpeptide angiotensin II receptor antagonists have been developed. Most of these are directed at the $AT_1$ receptor, but due to concerns about unbalanced activation of the $AT_2$ receptor, some newer angiotensin II receptor antagonists target both $AT_1$ and $AT_2$ receptors. Angiotensin II receptor antagonists are generally highly specific, having very little effect on other hormone receptors or ion channels.

Any orally active antagonists of the $AT_1$ angiotensin II receptor may be used in this invention. Some examples of angiotensin II receptor antagonists suitable for use herein are saralasin (including saralasin acetate), candesartan (including candesartan cilexetil), CGP-63170, EMD-66397, KT3-671, LRB/081, valsartan, A-81282, BIBR-363, BIBS-222, BMS-184698, CV11194, EXP-3174, KW-3433, L-161177, L-162154, LR-B/057, LY-235656, PD150304, U-96849, U-97018, UP-275-22, WAY-126227, WK-1492.2K, YM-31472, losartan (including losartan potassium), E-4177, EMD-73495, eprosartan, HN-65021, irbesartan, L-159282, ME-3221, SL-91.0102, tasosartan, telmisartan, UP-269-6, YM-358, CGP-49870, GA-0056, L-159689, L-162234, L-162441, L-163007, PD-123177, A81988, BMS-180560, CGP-38560A, CGP-48369, DA-2079, DE-3489, DuP-167, EXP-063, EXP-6155, EXP-6803, EXP-7711, EXP-9270, FK-739, HR-720, ICI D6888, ICI-D7155, ICI-D8731, isoteoline, KRI-1177, L-158809, L-158978, L-159874, LR B087, LY-285434, LY-302289, LY-315995, RG-13647, RWJ-38970, RWJ-46458, S-8307, S-8308, saprisartan, sarmesin, WK-1360, X-6803, ZD-6888, ZD-7155, ZD-8731, BIBS39, CI-996, DMP-811, DuP-532, EXP-929, L163017, LY-301875, XH-148, XR-510, zolasartan, and PD-123319.

Preferred angiotensin II receptor antagonists include losartan (which is the prototype and best known angiotensin II receptor antagonist), irbesartan, eprosartan, candesartan, valsartan, telmisartan, zolasartin, and tasosartan. Particularly preferred is losartan.

Renin inhibitors: Compounds that inhibit renin activity include: renin antibodies; analogs of the prosegment of renin; analogs of pepstatin; and analogs of the renin substrate angiotensinogen. As most of these compounds are peptides, they tend to have low oral bioavailability. Non-peptide renin inhibitors are of most interest in this invention. Preferred renin inhibitors are remikiren (Ro 42-5892), A-72517, and A-74273, with remikiren being most preferred.

C. ASPIRIN

Aspirin (acetylsalicylic acid), when administered in low daily doses over a long term to patients at risk for cardiovascular events, is well established to prevent myocardial infarction and strokes due to thrombosis. Second heart attacks, strokes, and cardiovascular deaths are reduced by at least 25% through the daily administration of low doses (approximately 80 mg) of aspirin.

A number of mechanisms are likely responsible for the cardiovascular protective activity of aspirin, but its antithrombotic, anti-platelet aggregating activities are probably highly significant in this regard. Aspirin irreversibly acetylates the enzyme cyclooxygenase, rendering it non-functional. Cyclooxygenase is essential to the synthesis of (among other compounds) prostaglandins, many of which are proinflammatory; thromboxane $A_2$, which is synthesized by platelets to promote platelet aggregation and ultimately thrombosis (blood clotting); and prostacyclins, which have anti-platelet aggregating properties. Cyclooxygenases are synthesized in endothelial cells and not in platelets. Low doses of aspirin neutralize cyclooxygenase selectively in the platelets, while allowing continued cyclooxygenase and prostacyclin synthesis in the endothelial cells. The net effect is to reduce inflammation and platelet aggregation, and thus thrombosis, in the blood vessels.

While aspirin is most preferred for use in this invention, other salicylates, including magnesium salicylate, and other anti-platelet aggregating agents, such as anagrelide, dipyridamole, clopidogrel, and ticlopidine, may also be used herein. Other cyclooxygenase inhibitors, including other nonsteroidal anti-inflammatory drugs (NSAIDS) such as ibuprofen, sulindac, sulindac sulfide, sulindac sulfone, flurbiprofen, indomethacin, naproxen, meclafenamic acid, and piroxicam, may also be used in this invention.

D. VITAMIN B COMPOUNDS

Elevated serum levels of homocysteine, an amino acid not found in proteins, is highly correlated with atherosclerosis, heart disease, stroke, and peripheral vascular disease. Many studies have shown that orally administered supplements of vitamin $B_6$ (also called pyridoxine), vitamin $B_{12}$ (also called cobalamin or cyanocobalamin), and folic acid (or folates) can lower homocysteine levels and reduce the incidence of atherosclerosis, myocardial infarction, and stroke. Folic acid and folates appear particularly potent in this regard. Recent surveys have found that approximately 88% of Americans have a daily intake of folic acid that is below the 400 micrograms per day that is recommended to maintain normal homocysteine levels. In the practice of this invention, folinic acid or folates may be used instead of folic acid, though folic acid is preferred. Folates that may be used include 5-methyl tetrahydrofolic acid (5MeTHF), tetrahydrofolic acid (THF), and 5-formyl tetrahydrofolic acid (5CHOTHF).

E. DERIVATIVES

Any of the active agents may be administered in the form of a salt, ester, amide, prodrug, active metabolite, analog, or the like, provided that the salt, ester, amide, prodrug, active metabolite, or analog is pharmaceutically acceptable and pharmacologically active in the present context. Salts, esters, amides, prodrugs, metabolites, analogs, and other derivatives of the active agents may be prepared using standard procedures known to those skilled in the art of synthetic organic chemistry and described, for example, by J. March, Advanced Organic Chemistry: Reactions, Mechanisms and Structure, 4th Edition (New York: Wiley-Interscience, 1992).

For example, acid addition salts are prepared from a drug in the form of a free base using conventional methodology involving reaction of the free base with an acid. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Conversely, preparation of basic salts of acid moieties that may be present on an active agent may be carried out in a similar manner using a pharmaceutically acceptable base such as sodium hydroxide, potassium hydroxide, ammonium hydroxide, calcium hydroxide, trimethylamine, or the like. Preparation of esters involves transformation of a carboxylic acid group via a conventional esterification reaction involving nucleophilic attack of an $RO^-$ moiety at the carbonyl carbon. Esterification may also be carried out by reaction of a hydroxyl group with an esterification reagent such as an acid chloride. Esters can be reconverted to the free acids, if desired, by using conventional hydrogenolysis or hydrolysis procedures. Amides may be prepared from esters, using suitable amine reactants, or they may be prepared from an anhydride or an acid chloride by reaction with ammonia or a lower alkyl amine. Prodrugs and active metabolites may also be prepared using techniques known to those skilled in the art or described in the pertinent literature. Prodrugs are typically prepared by covalent attachment of a moiety that results in a compound that is therapeutically inactive until modified by an individual's metabolic system.

Other derivatives and analogs of the active agents may be prepared using standard techniques known to those skilled in the art of synthetic organic chemistry, or may be deduced by reference to the pertinent literature. In addition, chiral active agents may be in isomerically pure form, or they may be administered as a racemic mixture of isomers.

III. PHARMACEUTICAL COMPOSITIONS AND DOSAGE FORMS:

Oral dosage forms are used to administer the combination of active agents, and include tablets, capsules, caplets, solutions, suspensions, and/or syrups, and may also comprise a plurality of granules, beads, powders, or pellets that may or may not be encapsulated. Such dosage forms are prepared using conventional methods known to those in the field of pharmaceutical formulation and described in the pertinent texts, e.g., in Gennaro, A. R., editor, Remington: The Science and Practice of Pharmacy, 20th Edition (Lippincott, Williams and Wilkins, 2000). Tablets and capsules represent the most convenient oral dosage forms, in which cases solid pharmaceutical carriers are employed.

Tablets may be manufactured using standard tablet processing procedures and equipment. One method for forming tablets is by direct compression of a powdered, crystalline, or granular composition containing the active agent(s), alone or in combination with one or more carriers, additives, or the like. As an alternative to direct compression, tablets can be prepared using wet-granulation or dry-granulation processes. Tablets may also be molded rather than compressed, starting with a moist or otherwise tractable material; however, compression and granulation techniques are preferred.

In addition to the active agent(s), then, tablets prepared for oral administration using the method of the invention will generally contain other materials such as binders, diluents, lubricants, disintegrants, fillers, stabilizers, surfactants, coloring agents, and the like. Binders are used to impart cohesive qualities to a tablet, and thus ensure that the tablet remains intact after compression. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, ethyl cellulose, hydroxyethyl cellulose, and the like), and Veegum. Diluents are typically necessary to increase bulk so that a practical size tablet is ultimately provided. Suitable diluents include dicalcium phosphate, calcium sulfate, lactose, cellulose, kaolin, mannitol, sodium chloride, dry starch, and powdered sugar. Lubricants are used to facilitate tablet manufacture; examples of suitable lubricants include, for example, magnesium stearate, calcium stearate, and stearic acid. Stearates, if present, preferably represent at no more than approximately 2 wt. % of the drug-containing core. Disintegrants are used to facilitate disintegration of the tablet, and are generally starches, clays, celluloses, algins, gums, or crosslinked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Stabilizers are used to inhibit or retard drug decomposition reactions that include, by way of example, oxidative reactions. Surfactants may be anionic, cationic, amphoteric, or nonionic surface active agents.

The dosage form may also be a capsule, in which case the active agent-containing composition may be encapsulated in the form of a liquid or solid (including particulates such as granules, beads, powders, or pellets). Suitable capsules may be either hard or soft, and are generally made of gelatin, starch, or a cellulosic material, with gelatin capsules preferred. Two-piece hard gelatin capsules are preferably sealed, such as with gelatin bands or the like. See, for example, *Remington: The Science and Practice of Pharmacy,* cited supra, which describes materials and methods for preparing encapsulated pharmaceuticals. If the active agent-containing composition is present within the capsule in liquid form, a liquid carrier is necessary to dissolve the active agent(s). The carrier must be compatible with the capsule material and all components of the pharmaceutical composition, and must be suitable for ingestion.

When two or more active agents are combined in a single pharmaceutical dosage form, possible interactions among the active agents, and among the active agents and the excipients, must be considered. Such consideration is well within the purview of those skilled in the art of pharmaceutical formulation. For example, aspirin is acidic and may react with basic compounds or alkali esters in such a way as to cause hydrolysis of the aspirin and/or degradation of the other compounds. Aspirin can, for example, react with acid labile compounds such as pravastatin to degrade them. The present composition thus encompasses pharmaceutical compositions wherein two or more of the active agents are separated from each other within the pharmaceutical dosage form, by, for example, separating potentially interacting compounds from each other within the pharmaceutical dosage form, as in separate flat layers of a tablet (e.g., a bilayer or trilayer tablet), concentric layers, coated beads or granules (which may be incorporated into a compressed tablet or into a capsule), and/or by using buffers (see, for example, U.S. Pat. No. 6,235,311). It will also be appreciated by those in the art that such dosage forms, wherein two or more active agents are physically separated from the other active agents, can be manufactured so that different active agents will have different release profiles, e.g., if one active agent is formulated with an enteric coating, another active agent is formulated in a sustained release matrix, and the like. Alternatively, non-reactive pharmaceutically active derivatives of one or more of the potentially interacting compounds may be used, such as using a neutral salicylate instead of aspirin.

Solid dosage forms, whether tablets, capsules, caplets, or particulates, may, if desired, be coated so as to provide for delayed release. Dosage forms with delayed release coatings may be manufactured using standard coating procedures and equipment. Such procedures are known to those skilled in the art and described in the pertinent texts, e.g., in Remington, supra. Generally, after preparation of the solid dosage form, a delayed release coating composition is applied using a coating pan, an airless spray technique, fluidized bed coating equipment, or the like. Delayed release coating compositions comprise a polymeric material, e.g., cellulose butyrate phthalate, cellulose hydrogen phthalate, cellulose proprionate phthalate, polyvinyl acetate phthalate, cellulose acetate phthalate, cellulose acetate trimellitate, hydroxypropyl methylcellulose phthalate, hydroxypropyl methylcellulose acetate, dioxypropyl methylcellulose succinate, carboxymethyl ethylcellulose, hydroxypropyl methylcellulose acetate succinate, polymers and copolymers formed from acrylic acid, methacrylic acid, and/or esters thereof.

Sustained release dosage forms provide for drug release over an extended time period, and may or may not be delayed release. Generally, as will be appreciated by those of ordinary skill in the art, sustained release dosage forms are formulated by dispersing a drug within a matrix of a gradually bioerodible (hydrolyzable) material such as an insoluble plastic, a hydrophilic polymer, or a fatty compound, or by coating a solid, drug-containing dosage form with such a material. Insoluble plastic matrices may be comprised of, for example, polyvinyl chloride or polyethylene. Hydrophilic polymers useful for providing a sustained release coating or matrix cellulosic polymers include, without limitation: cellulosic polymers such as hydroxypropyl cellulose, hydroxyethyl cellulose, hydroxypropyl methyl cellulose, methyl cellulose, ethyl cellulose, cellulose acetate, cellulose acetate phthalate, cellulose acetate trimellitate, hydroxypropylmethyl cellulose phthalate, hydroxypropylcellulose phthalate, cellulose hexahydrophthalate, cellulose acetate hexahydrophthalate, and carboxymethylcellulose sodium; acrylic acid polymers and copolymers, preferably formed from acrylic acid, methacrylic acid, acrylic acid alkyl esters, methacrylic acid alkyl esters, and the like, e.g. copolymers of acrylic acid, methacrylic acid, methyl acrylate, ethyl acrylate, methyl methacrylate and/or ethyl methacrylate, with a terpolymer of ethyl acrylate, methyl methacrylate, and trimethylammonioethyl methacrylate chloride (sold under the tradename Eudragit RS) preferred; vinyl polymers and copolymers such as polyvinyl pyrrolidone, polyvinyl acetate, polyvinylacetate phthalate, vinylacetate crotonic acid copolymer, and ethylene-vinyl acetate copolymers; zein; and shellac, ammoniated shellac, shellac-acetyl alcohol, and shellac n-butyl stearate. Fatty compounds for use as a sustained release matrix material include, but are not limited to, waxes generally (e.g., carnauba wax) and glyceryl tristearate.

IV. UTILITY AND ADMINISTRATION

The methods and compositions of this invention are directed at individuals who are at elevated cardiovascular risk, where cardiovascular risk comprises the potential for cardiac arrest, acute or chronic myocardial infarction, coronary heart disease, ischemia, stroke, peripheral vascular disease, claudication, worsening angina, restenosis, and/or atherosclerosis. Individuals who are at elevated cardiovascular risk include those with systemic lupus erythematosus; diabetes; angina pectoris; manifest coronary artery disease; hypertension; hypercholesterolemia; kidney disease; Chlamydia infection; Bartonella infection; obstructive pulmonary disease; who are on hemodialysis; who have received an organ transplant; who are obese; who are elderly; who have a family history of heart disease, atherosclerosis, or stroke; who are or have been cigarette smokers; or who have a history of myocardial infarction, transient ischemic attacks, stroke, atherosclerosis, or peripheral vascular disease.

Many individuals who are at elevated cardiovascular risk are not treated for this condition, commonly due to the lack of an effective, safe, and convenient therapy. For example, women with systemic lupus erythematosus are at increased risk of myocardial infarction and stroke, likely due to an increased propensity for premature atherosclerosis, but are rarely treated adequately to reduce these risks. As therapy would be chronic for individuals at elevated cardiovascular risk, probably for the life of the patient, it should be simple and convenient for the patient. A high compliance rate for chronic therapy is found when a drug is administered orally once per day, preferably at bedtime. In a preferred embodiment of the present invention, the combination of cholesterol-lowering agent, inhibitor of the renin-angiotensin system, aspirin, and optionally B vitamins, is comprised within a single unit-dose tablet or capsule for once-daily dosing, preferably at bedtime. The present invention thus addresses a major medical need by providing an effective, safe, simple, and convenient way to reduce the risk of cardiovascular events in patients at elevated cardiovascular risk, which has a high probability for patient compliance.

In a related embodiment of the invention, the pharmaceutical composition of the invention is administered to a patient suffering an acute myocardial infarction at the time of the MI or immediately thereafter. The compositions of the invention, when administered in this manner, are particularly useful for increasing the likelihood that a patient suffering an acute MI will survive the event.

It is strongly preferred that the active agents be administered in a single dosage form, as emphasized above. However, in some cases, a patient may be given each active agent in its own separate dosage form, or a combination of individual "combination" dosage forms containing two or more of the present active agents. When separate dosage forms are used, the cholesterol-lowering agent, the inhibitor of the renin-angiotensin system, the aspirin, and optionally the B vitamins can be administered at essentially the same time (concurrently), or at separately staggered times (sequentially). Optimum beneficial effects are achieved when the active blood level concentrations of each active agent are maintained at substantially the same time, meaning that simultaneous drug administration is generally preferred. Other dosing schedules, such as administering the cholesterol-lowering agent and the inhibitor of the renin-angiotensin system once per day and administering the aspirin once, twice, or more times per day, are also contemplated. A single oral dosage form comprising all the active agents is, however, much preferred. Such a dosage form provides convenience and simplicity for the patient, thus increasing the chances for patient compliance, especially in patients who already take multiple medications due to existing heart disease or other diseases.

Since three or more active agents are being used together in a combination therapy, the potency of each of the agents and the interactive effects achieved by combining them together must also be taken into account. A consideration of these factors is well within the purview of the ordinarily skilled clinician for the purpose of determining the therapeutically effective or prophylactically effective dosage amounts.

Preferred oral dosage forms contain a therapeutically effective unit dose of each active agent, wherein the unit dose is suitable for once-daily oral administration. The therapeutically effective unit dose of any particular active agent will depend, of course, on the active agent, the needs of the patient, and on other factors known to the prescribing physician. Those of ordinary skill in the art of pharmaceutical formulation can readily deduce suitable unit doses for various active agents. In general, however, the therapeutically effective unit dosages for each of the active agents are as follows:

Approximately 10 mg to approximately 80 mg, preferably approximately 25 mg to approximately 60 mg, of an HMG CoA reductase inhibitor selected from the group consisting of atorvastatin, fluvastatin, lovastatin, pravastatin, and simvastatin.

Approximately 1 mg to approximately 20 mg, preferably approximately 5 mg to approximately 15 mg, of an ACE inhibitor selected from the group consisting of captopril, enalapril, fosinopril, lisinopril, quinapril, ramipril, and trandolapril.

Approximately 20 mg to approximately 600 mg, preferably approximately 20 mg to approximately 150 mg, of aspirin.

Optionally, at least one of:

Approximately 25 mg to approximately 75 mg, preferably approximately 40 mg to approximately 60 mg, of vitamin $B_6$.

Approximately 0.25 mg to approximately 2 mg, preferably approximately 0.5 mg to approximately 1.5 mg, of vitamin $B_{12}$.

Approximately 0.5 mg to approximately 8 mg, preferably approximately 1.5 mg to approximately 5 mg, of folic acid.

In a particularly preferred embodiment, the active ingredients are as follows:

40 mg of pravastatin
10 mg of ramipril
81 mg of aspirin
50 mg of vitamin $B_6$
1 mg of vitamin $B_{12}$
3 mg of folic acid The formulations of the invention will be administered for as long as the patient is at elevated cardiovascular risk; very likely, this will be for a prolonged period and possibly for the life of the patient. Administration for a least one to two weeks is required for minimal benefit to be achieved. In addition to the preferred formulations designed for daily dosing, sustained release forms of such formulations may be employed, which may provide for dosing biweekly, weekly, monthly, or the like.

V. PACKAGED KITS

In another embodiment, a packaged kit is provided that contains a plurality of oral dosage forms for self administration; a container means, preferably sealed, for housing the dosage forms during storage and prior to use; and instructions for a patient to carry out drug administration. The instructions will typically be written instructions on a package insert, a label, and/or on other components of the kit, and the oral dosage forms are as described herein. Each dosage form may be individually housed, as in a sheet of a metal foil-plastic laminate with each dosage form isolated from the others in individual cells or bubbles, or the dosage forms may be housed in a single container, as in a plastic bottle. The present kits will also typically include means for packaging the individual kit components, i.e., the dosage forms, the container means, and the written instructions for use. Such packaging means may take the form of a cardboard or paper box, a plastic or foil pouch, etc.

It is to be understood that while the invention has been described in conjunction with the preferred specific embodiments thereof, that the foregoing description as well as the examples that follow are intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

EXPERIMENTAL

The practice of the present invention will employ, unless otherwise indicated, conventional techniques of pharmaceutical formulation and the like, which are within the skill of the art. Such techniques are fully explained in the literature. In the following examples, efforts have been made to ensure accuracy with respect to numbers used (e.g., amounts, temperatures, etc.) but some experimental error and deviation should be accounted for. Unless otherwise indicated, temperature is in degrees Celsius and pressure is at or near atmospheric pressure at sea level. All reagents were obtained commercially unless otherwise indicated.

EXAMPLE 1

A hard gelatin capsule formulation is prepared as follows. The following ingredients are used in each capsule:

| | |
|---|---|
| Pravastatin | 40 mg |
| Ramipril | 10 mg |
| Aspirin (in enteric coated granules) | 81 mg |
| Vitamin $B_6$ | 50 mg |
| Vitamin $B_{12}$ | 1 mg |
| Folic acid | 3 mg |
| Calcium carbonate | 50 mg |
| Magnesium oxide | 50 mg |
| Magnesium carbonate | 25 mg |
| Cornstarch | 25 mg |
| Magnesium stearate | 1 mg |

Aspirin is granulated and coated with an enteric polymer in an aqueous or non-aqueous system. Eudragit L-30D-55 containing 10–15% of diethyl phthalate (w/w) is used in an aqueous system. The coating suspension is prepared having solid contents of 10%–30%. To prepare the coating suspension, diethyl phthalate is added to the Eudragit L-30D-55 and the contents stirred until the diethyl phthalate is completely dissolved. This resulting suspension is diluted with water to obtain a suspension containing the desired proportion of solid contents. Using this enteric coating suspension, the aspirin particles are coated, for example, in a fluid bed coating system using a Wurster insert or with top spray coating, so that aspirin particles of enteric quality can be produced. The enteric coated particles are mixed with powders or granules of the other active agents and the mixtures are mixed and encapsulated in a hard gelatin capsule with the excipients. The quantity of the buffering agents (calcium carbonate, magnesium carbonate, magnesium oxide) can be adjusted as necessary to minimize gastrointestinal side effects and possible interactions between folic acid and the other active agents. It should be understood that these buffering agents can be replaced with other suitable buffering agents, if desired.

EXAMPLE 2

A tablet formulation is prepared as follows. The following ingredients are used in each tablet:

| | |
|---|---|
| Pravastatin | 40 mg |
| Ramipril | 10 mg |
| Aspirin (in enteric coated granules) | 81 mg |
| Vitamin $B_6$ | 50 mg |
| Vitamin $B_{12}$ | 1 mg |
| Folic acid | 3 mg |
| Calcium carbonate | 50 mg |
| Magnesium oxide | 25 mg |
| Magnesium carbonate | 25 mg |
| Microcrystalline cellulose | 25 mg |
| Lactose | 25 mg |
| Magnesium stearate | 1 mg |

The formulation is prepared as in Example 1, except that the mixture of ingredients is pressed into tablets using conventional pharmaceutical means.

EXAMPLE 3

The capsule formulation of Example 1 is used in a double-blind, placebo-controlled study of 250 subjects (N=250) who are at elevated cardiac risk. The subjects are divided into three groups: Group 1 ("Usual Care") (N=100) receives usual medical care and a daily placebo capsule; Group 2 ("Stepped-Up Risk Management") (N=100) receives usual medical care plus a daily capsule that contains 40 mg pravastatin; and Group 3 ("Aggressive Risk Management") receives usual medical care plus the capsule formulation of Example 1 for daily dosing.

Entry criteria for the study: All persons greater than 18 years old with systemic lupus erythematosus (SLE) as defined by the 1997 revised ACR criteria for SLE or who are diagnosed and followed by a member of the American College of Rheumatology will be eligible. The SLE manifestations/criteria will be recorded.

The following exclusion criteria will apply: liver disease; pregnancy, nursing, or unwillingness to use acceptable contraception; heavy alcohol consumption; concomitant cholestyramine, niacin, or erythromycin; aspirin intolerance; concomitant lithium; concomitant potassium supplement or potassium sparing diuretic; concomitant cyclosporin; history of allergy or sensitivity to ACE inhibitors; congestive heart failure; renal artery stenosis; peptic ulcer disease in last 6 months; history of intracranial bleed or brain tumor; bleeding diathesis; history of muscle disease; participation in study of another experimental agent.

The study will last five years. Approximately 10% of the subjects in each of the three groups will be given a blood pressure measuring machine and will measure and record their blood pressure once daily. Groups 2 and 3 will receive individualized patient education on reducing cardiovascular risk. Subjects in all the groups will receive the following laboratory tests:

Baseline: Blood pressure; ANA; C-reactive protein; antiphospholipid antibody; total, HDL, and LDL cholesterol; CBC; creatinine; potassium. Serum will be stored.

Three weeks: Blood pressure; SGPT; total, HDL, and LDL cholesterol; CBC; creatinine; potassium. Serum will be stored (1 red top).

Exit: Blood pressure; total, HDL, and LDL cholesterol; CBC; creatinine. Serum will be stored (1 red top).

At the completion of the study it is found that subjects in Group 2 had fewer cardiovascular events than those in Group 1, and that subjects in Group 3 had significantly fewer cardiovascular events than those in Group 2.

EXAMPLE 4

A study is conducted as in Example 3, except that the tablet formulation of Example 2 is used instead of the capsule formulation of Example 1. At the completion of the study it is found that subjects in Group 2 had fewer cardiovascular events than those in Group 1, and that subjects in Group 3 had significantly fewer cardiovascular events than those in Group 2.

EXAMPLE 5

A study is conducted as in Example 3, except that subjects in Group 1 receive four placebo capsules for daily dosing, subjects in Group 2 receive one capsule containing 40 mg pravastatin and three placebo capsules for daily dosing, and subjects in Group 3 receive one capsule containing 40 mg pravastatin, one capsule containing 10 mg ramipril, one capsule containing 81 mg aspirin, and one capsule containing 50 mg vitamin $B_6$, 1 mg vitamin $B_{12}$, and 3 mg folic acid for daily dosing. The subjects in all the groups are instructed to take their four capsules for daily dosing once per day at approximately the same time. At the completion of the study it is found that subjects in Group 2 had fewer cardiovascular events than those in Group 1, and that subjects in Group 3 had significantly fewer cardiovascular events than those in Group 2.

EXAMPLE 6

A tablet formulation is prepared as follows. The following ingredients are used in each tablet:

| | |
|---|---|
| Lovastatin | 50 mg |
| Enalapril | 15 mg |
| Aspirin | 81 mg |
| Vitamin $B_6$ | 50 mg |
| Vitamin $B_{12}$ | 1 mg |
| Folic acid | 3 mg |
| Lactose | 75 mg |
| Magnesium oxide | 25 mg |
| Microcrystalline cellulose | 25 mg |
| Stearic acid | 4 mg |

The powdered ingredients are mixed and formed into tablets by conventional pharmaceutical means.

We claim:

1. A method for treating a patient at an elevated cardiovascular risk, comprising orally administering, on a daily basis, a pharmaceutical composition consisting essentially of a combination of:
   (a) a therapeutically effective unit dosage of a cholesterol-lowering agent;
   (b) a therapeutically effective unit dosage of an inhibitor of the renin-angiotensin system;
   (c) a therapeutically effective unit dosage of aspirin;
   (d) at least one of vitamin $B_6$, vitamin $B_{12}$, and folic acid; and
   (e) a pharmaceutically acceptable carrier, wherein each of the therapeutically effective unit dosages is a therapeutically effective daily dose.

2. The method of claim 1, wherein the elevated cardiovascular risk is an elevated risk of cardiac arrest, myocardial infarction, coronary heart disease, ischemia, stroke, peripheral vascular disease, claudication, restenosis, and/or atherosclerosis.

3. The method of claim 1, wherein the patient has systemic lupus erythematosus.

4. The method of claim 1, wherein the patient is or has been a cigarette smoker.

5. The method of claim 1, wherein the patient is diabetic.

6. The method of claim 1, wherein the patient is on hemodialysis.

7. The method of claim 1, wherein the patient has received an organ transplant.

8. The method of claim 1, wherein the cholesterol-lowering agent is selected from the group consisting of HMG CoA reductase inhibitors, bile acid sequestrants, probucol, fibric acid agents, and combinations thereof.

9. The method of claim 8, wherein the cholesterol-lowering agent is an HMG CoA reductase inhibitor.

10. The method of claim 9, wherein the HMG CoA reductase inhibitor is selected from the group consisting of atorvastatin, cerivistatin, fluindostatin, fluvastatin, lovastatin, mevastatin, pravastatin, simvastatin, and velostatin.

11. The method of claim 10, wherein the HMG CoA reductase inhibitor is selected from the group consisting of lovastatin and pravastatin.

12. The method of claim 11, wherein the HMG CoA reductase inhibitor is pravastatin.

13. The method of claim 1, wherein the inhibitor of the renin-angiotensin system is selected from the group consisting of angiotensin converting enzyme (ACE) inhibitors and angiotensin II antagonists.

14. The method of claim 13, wherein the inhibitor of the renin-angiotensin system is an ACE inhibitor.

15. The method of claim 14, wherein the ACE inhibitor is selected from the group consisting of captopril, cilazapril, delapril, enalapril, fentiapril, fosinopril, indolapril, lisinopril, perindopril, pivopril, quinapril, ramipril, spirapril, trandolapril, and zofenopril.

16. The method of claim 15, wherein the ACE inhibitor is selected from the group consisting of captopril, enalapril, fosinopril, lisinopril, quinapril, ramipril, and trandolapril.

17. The method of claim 16, wherein the ACE inhibitor is ramipril.

18. The method of claim 13, wherein the inhibitor of the renin-angiotensin system is an angiotensin II antagonist.

19. The method of claim 18, wherein the angiotensin II antagonist is selected from the group consisting of losartan, irbesartan, eprosartan, candesartan, valsartan, telmisartan, zolasartin, and tasosartan.

20. The method of claim 19, wherein the angiotensin II antagonist is losartan.

21. The method of claim 1, wherein the pharmaceutical composition is administered in the form of a tablet, capsule, or caplet.

22. A method for treating a patient at an elevated cardiovascular risk, comprising orally administering, on a daily basis, a pharmaceutical composition comprising a combination of:
   (a) approximately 10 mg to approximately 80 mg of an HMG CoA reductase inhibitor selected from the group consisting of atorvastatin, fluvastatin, lovastatin, pravastatin, and simvastatin;
   (b) approximately 1 mg to approximately 20 mg of an ACE inhibitor selected from the group consisting of captopril, enalapril, fosinopril, lisinopril, quinapril, ramipril, and trandolapril;
   (c) approximately 20 mg to approximately 600 mg aspirin;
   (d) at least one of
      (i) approximately 25 mg to approximately 75 mg vitamin $B_6$,
      (ii) approximately 0.25 mg to approximately 2 mg vitamin $B_{12}$, and
      (iii) approximately 1 mg to approximately 8 mg folic acid; and
   (e) a pharmaceutically acceptable carrier.

23. A method for treating a patient at an elevated cardiovascular risk, comprising orally administering, on a daily basis, a pharmaceutical composition comprising a combination of:
   (a) approximately 10 to approximately 80 mg pravastatin;
   (b) approximately 1 to approximately 20 mg ramipril;
   (c) approximately 20 to approximately 150 mg aspirin;
   (d) approximately 25 mg to approximately 75 mg vitamin $B_6$;
   (e) approximately 0.25 mg to approximately 2 mg vitamin $B_{12}$;
   (f) approximately 1 mg to approximately 8 mg folic acid; and
   (g) a pharmaceutical acceptable carrier.

24. An orally administrable pharmaceutical formulation for treating a patient at an elevated cardiovascular risk, comprising a combination of:
   (a) a therapeutically effective unit dosage of a cholesterol-lowering agent;
   (b) a therapeutically effective unit dosage of an inhibitor of the renin-angiotensin system;
   (c) a therapeutically effective unit dosage of aspirin; and
   (d) at least one of vitamin $B_6$, vitamin $B_{12}$, and folic acid; and
   (e) a pharmaceutically acceptable carrier, wherein each of the therapeutically effective unit dosages is a therapeutically effective daily dose.

25. The formulation of claim 24, wherein the cholesterol-lowering agent is selected from the group consisting of HMG CoA reductase inhibitors, bile acid sequestrants, probucol, fibric acid agents, and combinations thereof.

26. The formulation of claim 24, wherein the cholesterol-lowering agent is an HMG CoA reductase inhibitor.

27. The formulation of claim 26, wherein the HMG CoA reductase inhibitor is selected from the group consisting of atorvastatin, cerivistatin, fluindostatin, fluvastatin, lovastatin, mevastatin, pravastatin, simvastatin, and velostatin.

28. The formulation of claim 27, wherein the HMG CoA reductase inhibitor is selected from the group consisting of lovastatin and pravastatin.

29. The formulation of claim 28, wherein the HMG CoA reductase inhibitor is pravastatin.

30. The formulation of claim 24, wherein the inhibitor of the renin-angiotensin system is selected from the group consisting of angiotensin converting enzyme (ACE) inhibitors and angiotensin II antagonists.

31. The formulation of claim 30, wherein the inhibitor of the renin-angiotensin system is an ACE inhibitor.

32. The formulation of claim 31, wherein the ACE inhibitor is selected from the group consisting of captopril, cilazapril, delapril, enalapril, fentiapril, fosinopril, indolapril, lisinopril, perindopril, pivopril, quinapril, ramipril, spirapril, trandolapril, and zofenopril.

33. The formulation of claim 32, wherein the ACE inhibitor is selected from the group consisting of captopril, enalapril, fosinopril, lisinopril, quinapril, ramipril, and trandolapril.

34. The formulation of claim 33, wherein the ACE inhibitor is ramipril.

35. The formulation of claim 30, wherein the inhibitor of the renin-angiotensin system is an angiotensin II antagonist.

36. The formulation of claim 35, wherein the angiotensin II antagonist is selected from the group consisting of losartan, irbesartan, eprosartan, candesartan, valsartan, telmisartan, zolasartin, and tasosartan.

37. The formulation of claim 36, wherein the angiotensin II antagonist is losartan.

38. The formulation of claim 34, wherein the pharmaceutical composition is administered in the form of a tablet, capsule, or caplet.

39. A formulation for treating a patient at an elevated cardiovascular risk, comprising a combination of:
   (a) approximately 10 to approximately 80 mg of an HMG CoA reductase inhibitor selected from the group consisting of atorvastatin, fluvastatin, lovastatin, pravastatin, and simvastatin;
   (b) approximately 1 to approximately 20 mg of an ACE inhibitor selected from the group consisting of captopril, enalapril, fosinopril, lisinopril, quinapril, ramipril, and trandolapril;
   (c) approximately 20 to approximately 600 mg aspirin;
   (d) at least one of
      (i) approximately 25 mg to approximately 75 mg vitamin $B_6$,
      (ii) approximately 0.25 mg to approximately 2 mg vitamin $B_{12}$, and
      (iii) approximately 1 mg to approximately 8 mg folic acid; and
   (e) a pharmaceutically acceptable carrier.

40. A formulation for treating a patient at an elevated cardiovascular risk, comprising a combination of:
   (a) approximately 10 to approximately 80 mg pravastatin;
   (b) approximately 1 to approximately 20 mg ramipril;
   (c) approximately 20 to approximately 150 mg aspirin;
   (d) approximately 25 mg to approximately 75 mg vitamin $B_6$;
   (e) approximately 0.25 mg to approximately 2 mg vitamin $B_{12}$;
   (f) approximately 1 mg to approximately 8 mg folic acid; and
   (g) a pharmaceutically acceptable carrier.

41. The formulation of claim 24, comprising a tablet.

42. The formulation of claim 24, housed in a capsule.

43. The formulation of claim 39, comprising a tablet.

44. The formulation of claim 39, housed in a capsule.

45. The formulation of claim 40, comprising a tablet.

46. The formulation of claim 40, housed in a capsule.

47. A packaged kit for a patient at an elevated cardiovascular risk to use in the self-administration of multiple oral dosage forms, the kit including a container housing a plurality of oral dosage forms and instructions for carrying out drug administration therewith, the improvement comprising incorporating in said oral dosage forms a combination of: a therapeutically effective daily dose of a cholesterol-lowering agent, a therapeutically effective daily dose of an inhibitor of the renin-angiotensin system, a therapeutically effective daily dose of aspirin and a therapeutically effective daily dose of at least one of vitamin $B_6$, vitamin $B_{12}$, and folic acid.

48. The packaged kit of claim 47, wherein said oral dosage forms each comprise:
   (a) approximately 10 to approximately 80 mg of an HMG CoA reductase inhibitor as the cholesterol-lowering agent, wherein the HMG CoA reductase inhibitor is selected from the group consisting of atorvastatin, fluvastatin, lovastatin, pravastatin, and simvastatin;
   (b) approximately 1 to approximately 20 mg of an ACE inhibitor as the inhibitor of the renin-angiotensin system, wherein the ACE inhibitor is selected from the group consisting of captopril, enalapril, fosinopril, lisinopril, quinapril, ramipril, and trandolapril;
   (c) approximately 20 to approximately 600 mg aspirin; and
   (d) a pharmaceutically acceptable carrier.

49. The packaged kit of claim 48, wherein each of said oral dosage forms further comprises:
   (e) at least one of
      (i) approximately 25 mg to approximately 75 mg vitamin $B_6$,
      (ii) approximately 0.25 mg to approximately 2 mg vitamin $B_{12}$, and
      (iii) approximately 1 mg to approximately 8 mg folic acid.

50. The packaged kit of claim 49, wherein the HMG CoA reductase inhibitor is pravastatin and the ACE inhibitor is ramipril.

51. The packaged kit of claim 50, wherein each of said oral dosage forms contains approximately 25 mg to approximately 75 mg vitamin $B_6$, approximately 0.25 mg to approximately 2 mg vitamin $B_{12}$, and approximately 1 mg to approximately 8 mg folic acid.

52. A method for increasing the likelihood that a patient suffering an acute myocardial infarction will survive, comprising administering the pharmaceutical composition of claim 39 to the patient at the time of the acute myocardial infarction or immediately thereafter.

* * * * *

UNITED STATES PATENT AND TRADEMARK OFFICE
CERTIFICATE OF CORRECTION

PATENT NO. : 6,576,256 B2 Page 1 of 1
DATED : September 10, 2003
INVENTOR(S) : Liang, M. et al.

It is certified that error appears in the above-identified patent and that said Letters Patent is hereby corrected as shown below:

Column 1,
Line 7, the following two sentences should be inserted:
-- Statement of Rights
This invention was made with government support under grant R21AR47487 and grant 1P60AR47782 awarded by the National Institutes of Health. The government has certain rights in the invention. --

Signed and Sealed this

Fifteenth Day of June, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,576,256 B2 Page 1 of 1
DATED : June 10, 2003
INVENTOR(S) : Matthew H. Liang and JoAnn E. Manson It is certified that error appears in the above-identified patent and that said Letters Patent is hereby corrected as shown below:

Column 1,
Line 7, insert:
-- ACKNOWLEDGEMENT OF GOVERNMENT INTEREST
This invention was made with United States government support under Grant Nos. R21 AR 47487 and 1p60 AR 47782 awarded by the National Institute of Health. --.

Signed and Sealed this

Twenty-seventh Day of December, 2005

JON W. DUDAS
*Director of the United States Patent and Trademark Office*